United States Patent [19]

Sridhar

[11] Patent Number: 4,652,343
[45] Date of Patent: Mar. 24, 1987

[54] PROCESS FOR THE SEPARATION OF MIXTURES OF PARAFFIN OR RESPECTIVELY PARAFFINS OF 6-14 CARBON ATOMS AND ALCOHOL OR RESPECTIVELY ALCOHOLS OF 4-8 CARBON ATOMS

[75] Inventor: Srinivasan Sridhar, Marl, Fed. Rep. of Germany

[73] Assignee: Chemische Werke Huls Aktiengesellschaft, Marl, Fed. Rep. of Germany

[21] Appl. No.: 724,120

[22] Filed: Apr. 17, 1985

Related U.S. Application Data

[63] Continuation of Ser. No. 462,228, Jan. 31, 1983, abandoned.

[30] Foreign Application Priority Data

Feb. 2, 1982 [DE] Fed. Rep. of Germany ....... 3203440

[51] Int. Cl.⁴ ............................................. B01D 3/36
[52] U.S. Cl. ...................................... 203/53; 203/55; 203/63; 203/70; 203/75; 203/76; 203/77; 203/93; 260/513 R; 568/913; 585/802; 585/868
[58] Field of Search ........................ 203/92, 93, 95-97, 203/55, 53, 56, 75, 76, 77, 82, 83, 63, 70; 585/802, 868; 568/913; 260/513 R

[56] References Cited

U.S. PATENT DOCUMENTS

| | | |
|---|---|---|
| 2,386,058 | 10/1945 | Patterson et al. ..................... 203/53 |
| 2,480,652 | 8/1949 | Hillman et al. ....................... 203/83 |
| 2,617,757 | 11/1952 | Michael ................................. 203/53 |
| 2,663,682 | 12/1953 | Traeger et al. ....................... 203/55 |
| 2,666,736 | 1/1954 | Robertson et al. .................. 203/53 |
| 2,891,891 | 6/1959 | Stewart et al. ....................... 203/76 |
| 3,485,879 | 12/1969 | Mamerviskis et al. ............. 585/802 |
| 3,689,375 | 9/1972 | Furukawa et al. ................. 585/868 |

FOREIGN PATENT DOCUMENTS

| 1358095 | 6/1974 | United Kingdom . |
|---|---|---|
| 1588363 | 4/1981 | United Kingdom . |

Primary Examiner—Wilbur Bascomb
Attorney, Agent, or Firm—Antonelli, Terry & Wands

[57] ABSTRACT

The separation of homozeotropic mixtures of a paraffin or paraffins of 6-14 carbon atoms and an alcohol or alcohols of 4-8 carbon atoms is conducted in two rectification steps. In a first step, rectification is carried out in the presence of water as the azeotropic agent, and the resultant distillate, after condensation, is separated into two liquid phases. The thus-obtained organic phase is rectified in a further step without the addition of water, and the head product consisting of an alcohol/paraffin mixture is recycled into the first step. The paraffin or paraffins and the alcohol or alcohols are obtained in the lower section of the individual rectifying step or steps. The water which may be present in the starting mixture is removed from the cycle. Low-boiling paraffins and/or low-boiling alcohols are suitable as additional azeotropic agents.

13 Claims, 5 Drawing Figures

PROCESS FOR THE SEPARATION OF MIXTURES OF PARAFFIN OR RESPECTIVELY PARAFFINS OF 6–14 CARBON ATOMS AND ALCOHOL OR RESPECTIVELY ALCOHOLS OF 4–8 CARBON ATOMS

This is a continuation of application Ser. No. 462,228, filed Jan. 31, 1983, and now abandoned.

BACKGROUND OF THE INVENTION

In the distillatory separation of volatile compounds from a compound mixture, chemical engineers are frequently confronted with the case that the compounds possess equal volatility; i.e., form an azeotrope. As a result, these compounds are again present as a mixture in the distillate. If two of such equally volatile compounds are immiscible in the liquid phase (heteroazeotrope), they can be readily separated from each other. However, compounds miscible with each other (homoazeotrope) can be separated in the distillate only with great difficulties according to the state of the art.

The separation of homoazeotropic mixtures made up of a $C_6$–$C_{14}$ paraffin or paraffins and a $C_4$–$C_8$ alcohol or alcohols is of great interest for various industrial processes, such as, for example, for the processing of alkanesulfonic acids.

Alkanesulfonic acids are produced, inter alia, by the sulfoxidation of paraffins in the presence of water and sulfur dioxide under the effect of light. After the reaction, a large portion of the unreacted paraffins separates in the product discharged from the reactor as a paraffin phase and can be directly recycled into the reactor.

After exhausting residues of sulfur dioxide and oxygen in the gaseous phase, the remaining product contains alkanesulfonic acids, water, paraffins, and sulfuric acid (by-product).

Several methods have been proposed for the processing of this reaction product. It is known from DOS (German Unexamined Laid-Open Application) No. 2,139,477 (page 7), which application corresponds to British Pat. No. 1,358,095, to utilize an oxygen-containing, polar organic extractant immiscible with the hydrocarbons, such as methanol, ethanol, or a low-molecular weight ester. By this polar auxiliary medium, unmixing of the mixture is effected into a paraffin phase and a paraffin-free, aqueous organic phase. The aqueous organic phase contains the alkanesulfonic acids and the sulfuric acid. After separation of the residual paraffins, again as a separate phase, the sulfuric acid is then separated as the sulfate from the aqueous phase by neutralization with an alkaline hydroxide. The presently obtained alkanesulfonates are isolated as a melt by distillation.

According to the process of DOS No. 2,139,477, a weakly polar alcohol of at least 5 carbon atoms is used as the auxiliary medium. In this case, the sulfonic acids and the paraffin are transferred into the alcohol phase, and the aqueous phase contains the entire sulfuric acid and can be separated as such. The expense of neutralizing the sulfuric acid and filtration of the sulfate according to the method disclosed in DOS No. 2,139,477 (page 7) is thus avoided. With respect to separation of the paraffins and recovery of the alcohol, the possibility is also pointed out (page 7) that the alcohol and, in some cases, the paraffins can be distilled off azeotropically with the aid of a third component; however, the further separation of such azeotropes into individual compounds is not disclosed. Moreover, in the later DOS No. 2,745,691 (corresponding to British Pat. No. 1,588,363) by the same inventors and the same assignee, precisely this circumstance is even cited as a disadvantage of the process, since—so it is stated—difficulties are encountered in using the disclosed alcohols because they exhibit a similar volatility as the feed paraffins. Furthermore, in case of homoazeotropic mixtures, separation has been possible, as discussed above, only with the aid of expensive methods, such as extraction or multistage distillation under differing pressures.

The objective thus evolving is to find a process making it possible to separate homoazeotropic mixtures made up of a mixture of a $C_6$–$C_{13}$ paraffin or paraffins and a $C_4$–$C_8$ alcohol or alcohols.

BRIEF SUMMARY OF THE INVENTION

This object has been attained according to the invention by a process for the separation of such homoazeotropic mixtures which is conducted in two rectification steps.

It has been found, surprisingly, that separation of these homoazeotropic mixtures into two streams made up of pure compounds is possible in two rectifying steps by processing the compound streams in accordance with this invention. In one step, rectification is carried out in the presence of water as the azeotropic agent. If the feed does not contain adequate amounts of water as the azeotropic agent, additional water is supplied. Further suitable azeotropic agents are low-boiling paraffins; e.g., methane, ethane and propane and/or low-boiling alcohols; e.g., methanol and ethanol. If higher paraffins of more than 14 carbon atoms are contained in the mixture, they remain almost exclusively in the sump of this column. The resultant distillate is separated after condensation into two liquid phases. The thus-produced organic phase is rectified in a further step without the addition of water, and the head product, consisting of an alcohol-paraffin mixture, is recycled into the first step. The alcohol is obtained in the lower section of the column wherein, in the vapor phase, the proportion of paraffin to alcohol is higher, and the paraffin or paraffins are obtained in the lower section of the column wherein, in the vapor phase, the proportion of paraffin to alcohol is smaller.

BRIEF DESCRIPTION OF THE DRAWINGS

The invention will be further understood from the following description and the accompanying drawings wherein.

DETAILED DESCRIPTION OF THE INVENTION

Figure 1:
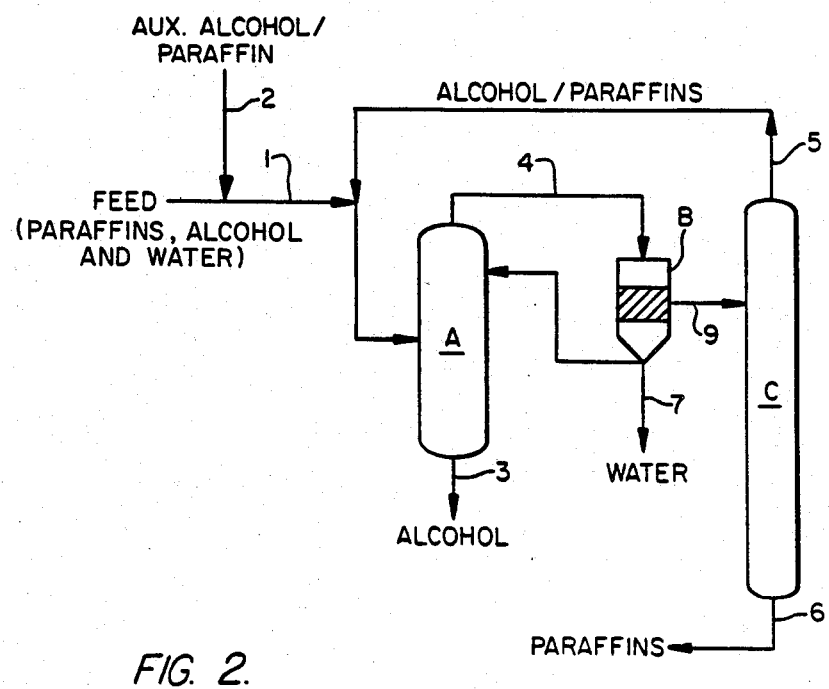
FIGS. 1–5 are schematic arrangements of the apparatus for effecting different embodiments of the process of this invention.
Figure 2:
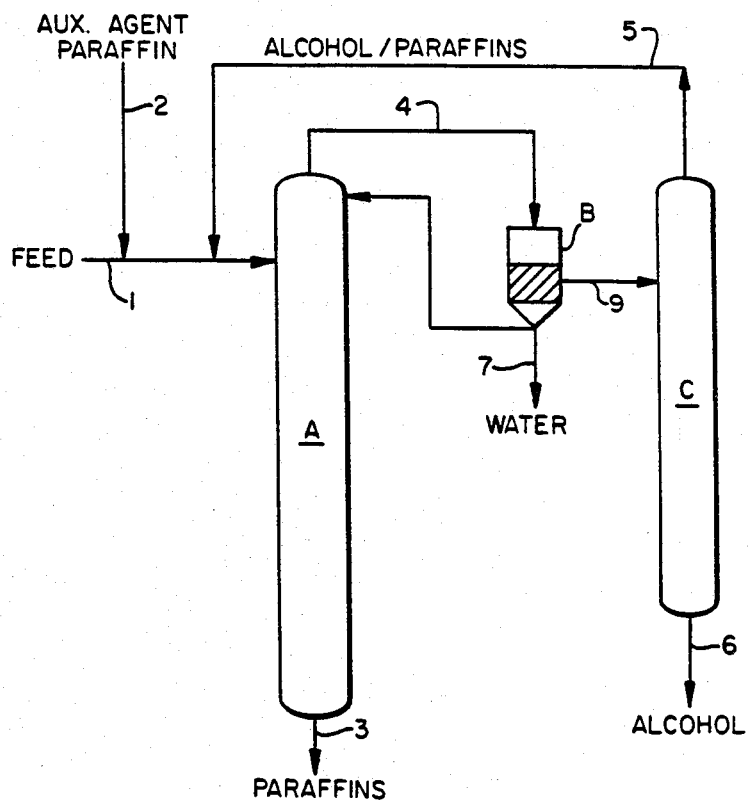
Figure 3:
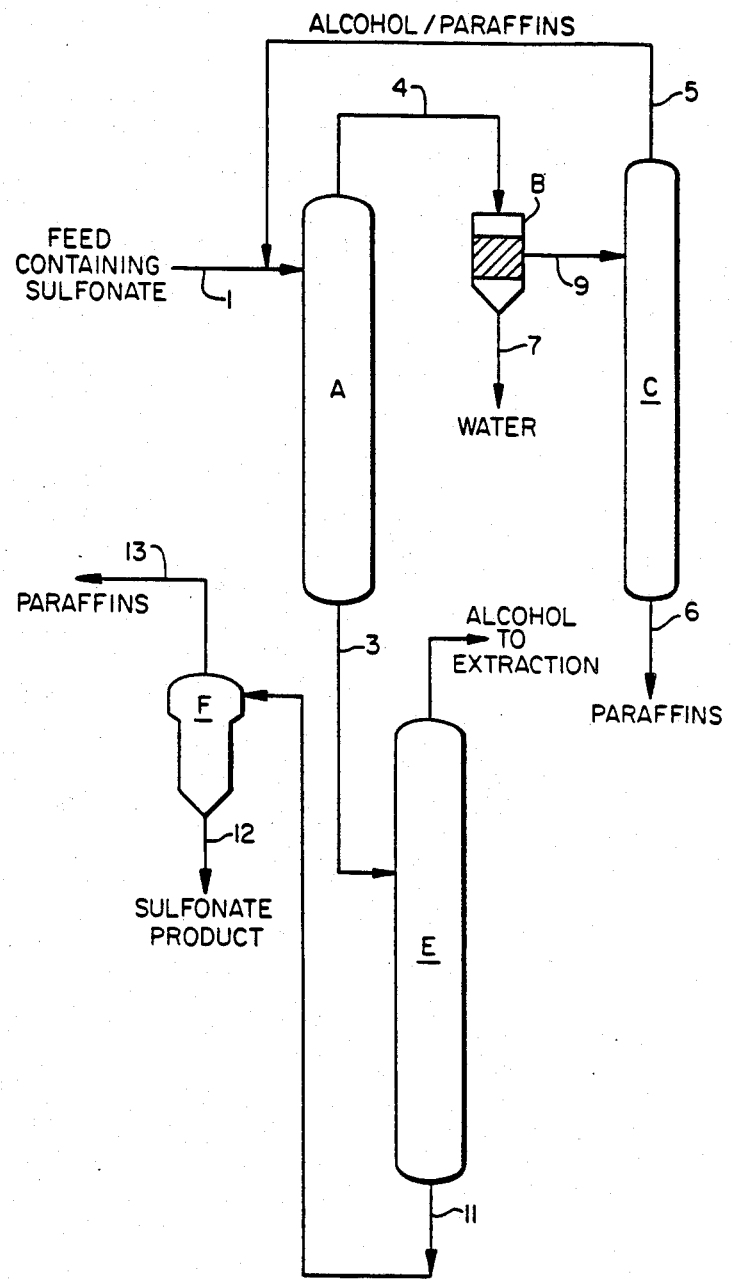
Figure 4:
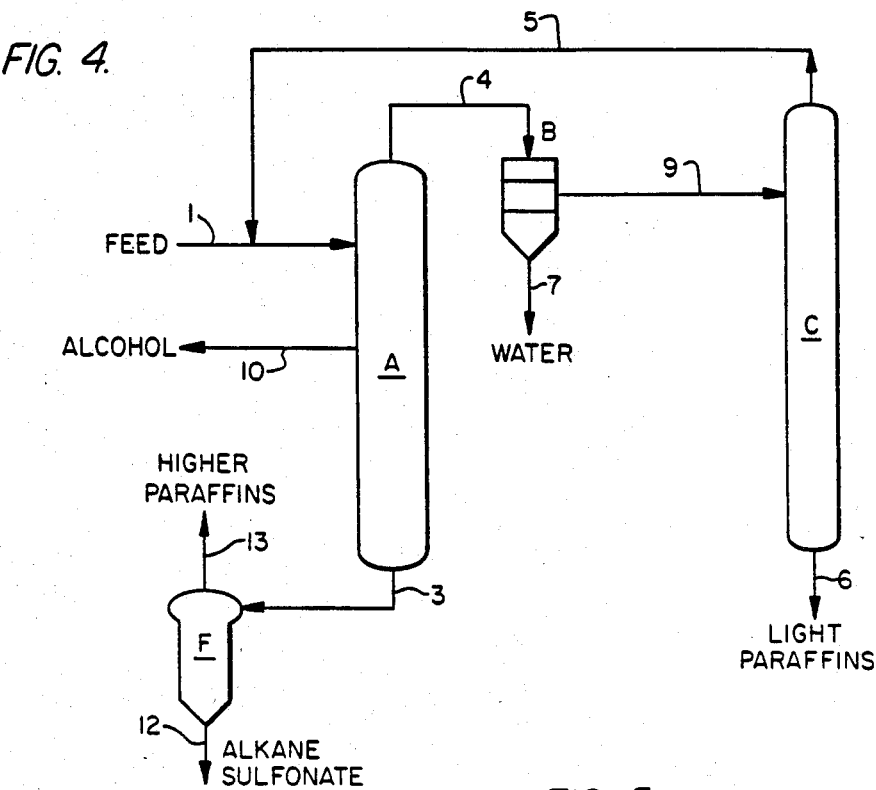
Figure 5:
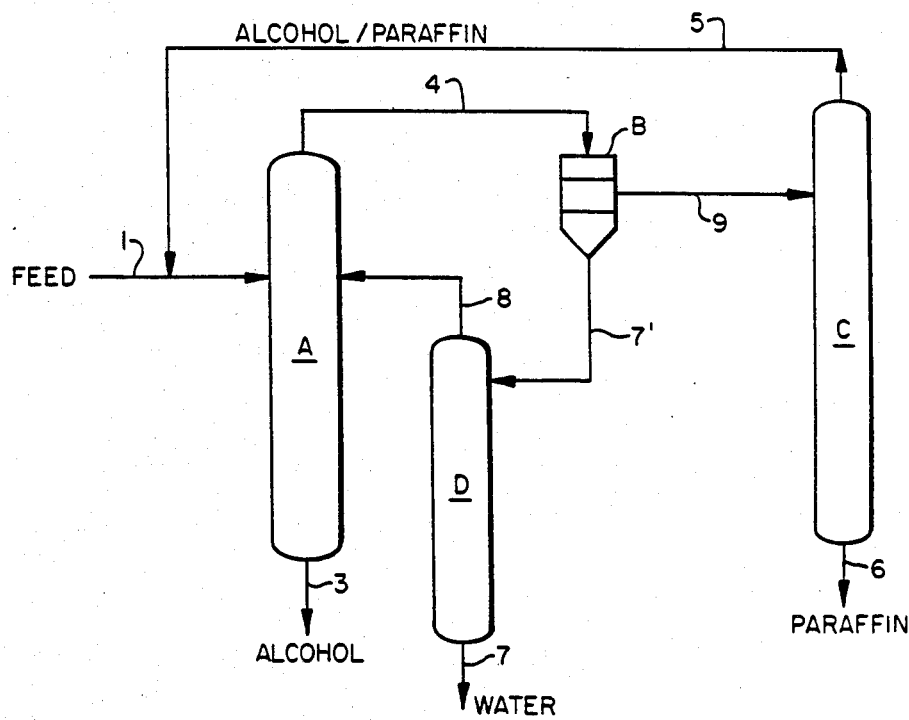

;p The process can be conducted continuously and discontinuously. The discontinuous mode of operation is especially suitable in case of relatively small quantities. Preferably, the process is conducted continuously.

An essential factor for the separation is that the quantitative ratio of paraffin to alcohol is different in the distillates of the two columns. If this ratio of paraffin to alcohol is the same in both columns, then varying quantitative ratios of paraffin to alcohol are obtained by altering the pressure.

The system containing ethylhexanol and $C_{10}$–$C_{13}$ paraffins represents a homoazeotropic mixture. According to this invention, the mixture is distilled in the presence of water, optionally after the addition of water, for example, at 100 mbar overhead, and is separated after condensation into two liquid phases. After separating the water from the distillate as the bottom phase, the almost anhydrous organic phase consisting of the $C_{10}$–$C_{13}$ paraffins and ethylhexanol is subjected to a further distillation, and the distillate is returned into the feed of the first distillation. With a continuous operation, pure ethylhexanol is obtained in the sump of the first distillation column, and the pure $C_{10}$–$C_{13}$ paraffins are found in the sump of the second column.

The system hexane/butanol, likewise, involves a homoazeotropic mixture. With the separation, according to this invention, at 1 bar, using the continuous mode of operation, the pure hexane is obtained in the sump of one distillation column, and pure butanol is obtained in the sump of the other column.

In case of $C_6$–$C_{14}$ paraffin mixtures, the lowest-boiling paraffin, or the low-boiling paraffins, can partially pass overhead together with the alcohol in the column wherein the organic phase is distilled. This mixture, according to the invention, is recycled into the preceding column wherein distillation is conducted in the presence of water. In the steady state condition, the entire amount of introduced $C_6$–$C_{14}$ paraffin is obtained in the sump of the column. In order to reach this stationary condition more easily and rapidly, these low-boiling compounds are preferably added to the cycle (as described in Example 3). It is also possible to add low-boiling paraffins not contained in the feed paraffin (as described in Example 2).

The amount of water to be used is generally 1–1,000, preferably 5–100% by weight, based on the paraffin present in this rectifying step. Optionally, the water separated after the distillation of the ternary mixture and condensation of the vapor is entirely or partially recycled into this distillation. Also, if desired, the alcohols and/or paraffins obtained after the separating step can be partially recycled into the rectification. It is also possible to recycle only the organic phase and to remove the aqueous phase.

Distillation is carried out under normal pressure or under a vacuum; in case of the higher homologs, the first distillation is conducted preferably at 50–400 mbar, especially at 100–300 mbar, and the second distillation is conducted preferably at 50–1,013 mbar, especially at 75–1,013 mbar.

Surprisingly, the separation of homoazeotropic mixtures of $C_6$–$C_{14}$ paraffins and $C_4$–$C_8$ alcohols, according to this invention, makes it superfluous to perform the heretofore required, expensive separation operation, such as by extraction or multistage distillation under varying pressures.

The process is of special interest for the separation of homoazeotropic mixtures as obtained when processing alkanesulfonic acids. The method of this invention simplifies this processing operation considerably.

EXAMPLE 1 (FIG. 1)

The 6th separation stage (from the bottom) of a distillation column A having 8 theoretical separating stages is charged with a mixture of $C_{10}$–$C_{13}$ paraffins, ethylhexanol, and water having the following composition (stream 1):
  n-decane: 43.3 kg/h
  undecane: 3.8 kg/h
  dodecane: 21.7 kg/h
  tridecane: 7.2 kg/h
  water: 1.0 kg/h
  2-ethylhexanol: 23.0 kg/h Container B is filled to the half-way mark with water at the beginning of the distillation, this water being introduced into column A as additional feed at the 6th separating stage (from the bottom). Once the distillate is obtained, the aqueous phase from B is, furthermore, completely recycled. Only after the temperature at the 4th separating stage of A has reached 80° C. and at the 7th separating stage, 45° C. is the additional removal step (stream 7) begun. Furthermore, initially 383 kg/h of a mixture composed of 85% by weight of n-decane and 15% by weight of 2-ethylhexanol is admixed to stream 1; namely, only until, in column C, the temperature has risen, at the 17th stage and at the 10th stage from the bottom, respectively, to 99° C. and 110° C. (via stream 2).

Distillation is carried out with a reflux ratio of 0.5 and under a pressure of 100 mbar. The distillate, consisting of a mixture (stream 4) of $C_{10}$–$C_{13}$ paraffins, water, and ethylexanol, has the following composition:
  n-decane: 386.0 kg/h
  undecane: 3.8 kg/h
  dodecane: 21.7 kg/h
  tridecane: 7.2 kg/h
  water: 652.7 kg/h
  2-ethylhexanol: 57.9 kg/h
(head temperature 44°–45° C.).

The pure alcohol (stream 3) is withdrawn from the sump of the column.

The distillate from column A is condensed at normal temperature and introduced into the separating vessel (B) wherein it is separated into a lower aqueous phase and an upper organic phase consisting of $C_{10}$–$C_{13}$ paraffins and 2-ethylhexanol. The water is, in part, returned into column A. The high water content in the vapor of the column is ensured in this way. However, the amount of water corresponding to the quantity in stream 1 is removed from the cycle (stream 7).

The organic phase is fed to the 15th stage of a further column C having 18 separating stages, wherein the $C_{11}$–$C_{13}$ paraffins are separated from the remaining compounds under 100 mbar/99° C. at the head and under a reflux ratio of 3. The head product (stream 5), consisting of 326 kg/h of n-decane besides 58 kg/h of ethylhexanol is reintroduced into the feed stream 1 of column A. The following compounds are withdrawn from the sump of column C (stream 6):
  n-decane: 43.3 kg/h
  undecane: 3.8 kg/h
  dodecane: 21.7 kg/h
  tridecane: 7.2 kg/h

EXAMPLE 2 (FIG. 1)

The mixture (stream 1) consists of:
  undecane: 12.0 kg/h
  dodecane: 6.0 kg/h
  2-ethylhexanol: 82.0 kg/h Processing takes place analogously to Example 1, including 65 kg of n-decane per hour in the distillation as a low-boiling auxiliary agent: The mixture is recycled to the 5th stage of column A. The column has 7 separating stages with a reflux of 123.22 kg/h of water. Distillation takes place at 100 mbar. The vapor (head temperature 43°–44° C.) has the following composition:
  decane: 65.12 kg/h
  undecane: 12.00 kg/h dodecane: 6.00 kg/h
water: 123.22 kg/h
2-ethylhexanol: 11.38 kg/h wherein the high water content or decane content, according to Example 1, is maintained; namely, by a one-time addition and without removal of water from container B. The control temperatures at 115° and 45° C., respectively, at the 2nd stage and 6th stage of column A, and 110° and 100° C., respectively, at the 5th stage and 18th stage of column C. The organic phase is fed to the 13th separating stage of column C (in total, 20 separating stages; reflux ratio 3; 99° C./100 mbar at the head). The decane stream is recirculated between the distillates of columns C, A, and the organic phase in separating vessel B. Withdrawal of alcohol and paraffin, respectively, takes place according to Example 1.

EXAMPLE 3 (FIG. 1)

A mixture of the following composition
undecane: 4.00 kg/h
dodecane: 2.00 kg/h
2-ethylhexanol: 68.00 kg/h and
water: 0.50 kg/h is introduced into the 8th separating stage from the bottom of a column A having 13 theoretical separating stages (reflux 24.2 kg/h water), and distillation is conducted under 300 mbar (head temperature 68° C.): The vapor consists of
undecane: 8.23 kg/h
dodecane: 2.00 kg/h
2-ethylhexanol: 5.05 kg/h and
water: 24.70 kg/h wherein the excess of undecane is added once to the system in correspondence with Example 1. The stream 1 is supplied with 4.23 kg/h of undecane and 5 kg/h of 2-ethylhexanol until the temperatures at the head and at the 10th stage from the bottom of column C have risen, respectively, to 140°-145° C. Additional control temperatures are 140° and 70° C., respectively, at the 3rd and 11th stages of column A. The vapor is condensed at normal temperature. The amount of water from separating vessel B corresponding to the fresh feed (0.5 kg/h) is continuously removed. The organic phase is fed to the 23rd stage (from the bottom) of a column having 40 separating stages and is distilled at 300 mbar/140° C. at the head with a reflux ratio of 15.

The feed paraffins and alcohol are withdrawn according to Example 1.

EXAMPLE 4 (FIG. 1)

A mixture of undecane and hexanol having the following composition:
undecane: 50.00 kg/h
n-hexanol: 50.00 kg/h is fed to the 5th separating stage from the bottom of a column A having 7 separating stages, and distillation is carried out under 300 mbar and in accordance with Example 3. At the beginning, a feed stream is combined with a mixture of 14% by weight of undecane and 86% by weight of n-hexanol (via stream 2) as in Example 1. The vapor (head temperature 67° C.) has the composition:
undecane: 61.8 kg/h
hexanol: 74.8 kg/h
water: 190.3 kg/h Water is added as described in Example 2. (The feed of the water from B is terminated once the temperature at the 3rd separating stage and the 6th separating stage, respectively, from the bottom in column A has risen to 140° C. and 70° C., respectively.) Additional control temperatures are 145° C. at the 5th and 30th stages of column C, respectively. The condensation of the vapor and the removal of the paraffin and alcohol take place according to Example 1. Column C has 33 separating stages (feed at the 19th plate from the bottom) with a reflux ratio of 10 and under 300 mbar (head temperature 123° C.). The distillate from column C corresponds to 11.8 kg/h of undecane, 74.8 kg/h of alcohol, and about 1 kg/h of water.

EXAMPLE 5 (FIG. 1)

A mixture of undecane and heptanol of the following compositions:
undecane: 85.0 kg/h
n-heptanol: 15.0 kg/h is, likewise, separated in accordance with Example 4. Initially, the feed stream is combined with a mixture of 38% by weight of undecane and 62% by weight of n-heptanol. The first distillation takes place at 300 mbar under conditions according to Example 4. The vapor has the composition
undecane: 146.6 kg/h
heptanol: 63.6 kg/h
water: 328.5 kg/h Column C has 44 separating stages with a reflux ration of 30 and under 100 mbar (head temperature 106° C.). The distillate corresponds to 61.6 kg/h of undecane besides 63.6 kg/h of alcohols and a small amount of water. The feed is introduced at the 30th separating stage (from the bottom). Paraffin and alcohol are withdrawn according to Example 3. Control temperatures are 70° and 140° C. at the $2^{nd}$ and $6^{th}$ stage of column A at the $5^{th}$ stage of column C.

EXAMPLE 6 (FIG. 3)

The compound stream contains the components of Example 3 and, additionally:
tridecane: 0.5 kg/h
higher paraffins: 0.5 kg/h
alkanesulfonate and other salts: 16.0 kg/h
water: 24.7 kg/h (in total).

The separation of the concomitantly boiling alcohol and the light paraffin is conducted by way of units A, B, and C in accordance with Example 3, but without recycling of stream 7.

The alcohol remaining in the sump stream 3 of column A is distilled off in a further column E under 100 mbar and with a reflux ratio of 0.5, and recycled into the extraction stage for separating sulfuric acid from the reactor efflux of the sulfoxidation. Column E has 16 separating stages with feed being introduced at the 12th stage from the bottom (head temperature 118° C.). The higher paraffins remaining in the sump stream 11 of column E are distilled off in a thin-film evaporator. The alkanesulfonate product exists from the sump of the thin-film evaporator (F).

EXAMPLE 7 (FIG. 4)

The feed stream 1 corresponds to stream 1 of Example 6. The mixture is introduced into the 21st stage of a column A having 26 separating stages, and the water is distilled off overhead under 300 mbar and with a reflux ratio of 1. The alcohol is withdrawn as a secondary stream from the 8th stage below the feed point. Otherwise, the example corresponds to Examples 1 and 6, respectively.

EXAMPLE 8 (FIG. 1)

A mixture having the following composition:
n-hexane: 50.00 kg/h
tert-butanol: 50.00 kg/h
is distilled according to Example 4 in the presence of 40 kg/h of water phase in the cycle at the head of the column A. The feed of water from B is terminated once the temperature at the 7th and 24th separating stages from the bottom of column A has risen to 83° C. and 60° C., respectively. Column A has 25 separating stages with feed being introduced to the 19th stage from the bottom. Column C has 30 separating stages with feed being introduced to the 18th stage from the bottom. Both distillations take place under normal pressure. The paraffin and alcohol, respectively, are withdrawn analogously to Example 1. The paraffin is 98% strength (2% by weight of butanol). The alcohol is pure (<0.3% by weight of hexane). A further control temperature is 65° C. at the 7th stage of column C.

EXAMPLE 9 (FIG. 5)

A mixture having the following composition:
n-hexane: 30.00 kg/h
tert-butanol: 67.00 kg/h and
water: 3.00 kg/h
is distilled according to Example 8 (5.2 kg/h of water in the cycle at the head of column A). The water included with the feed is conventionally separated, starting with the water phase in vessel B, by way of a stripping column D (stream 7). Column D is operated under normal pressure (head temperature 80° C.) and with a reflux ratio of 10. This column has 25 separating stages with feed to the 18th stage from the bottom. The alcohol-containing distillate from D (stream 8) is recycled into column A. Otherwise, the example corresponds to Example 8. The reflux of the organic phase from column A is 604 kg/h.

EXAMPLE 10 (FIG. 2)

A mixture having the composition:
n-hexane: 93.00 kg/h and
tert-butanol: 7.00 kg/h
is distilled according to Example 8. The feed of water from B is terminated once the temperature at the 7th separating stage from the bottom of column A has risen to 66° C. Column A is operated with reflux of the water phase and, additionally, with 1,120 kg/h of organic phase (head temperature 59° C./normal pressure). This column has 35 separating stages with feeding at the 25th stage from the bottom. The relationships in column C are 30 separating stages (feed to the 20th stage) with a reflux ratio of 3 and under the conditions of 32° C. at the head/300 mbar operating pressure. In contrast to the preceding examples and in contrast to FIG. 1, the paraffin is withdrawn from the sump of column A and the alcohol is withdrawn from the sump of column C. An additional control temperature is 56° C. at the 7th stage of column C.

EXAMPLE 11 (FIG. 1)

A mixture having the composition:
n-octane: 50.00 kg/h and
tert-butanol: 50.00 kg/h
is distilled in a preliminary stage (not shown in the figures)—in a columne D—to remove only the homoazeotrope. In the sump remains 48.6 kg/h of octane. Column D has 30 separating stages (feed at the 17th stage) and has the following operating conditions: reflux ratio 5, normal pressure, and head temperature 82° C. The distillate is redistilled according to Example 8 in the presence of 1.8 kg/h of water phase in the cycle at the head of column A. Recycling of the water phase from B is terminated once the temperature at the 5th stage from the bottom of column A has risen to 55° C. The column is operated under a reflux ratio of 30 (head temperature 49° C./300 mbar). This column has 50 separating stages with feed being introduced to the 25th stage. The water phase in vessel B is especially small as compared with the upper, organic phase. The relationships in column C are 25 separating stages (feed at 12th stage) with a reflux ratio of 20 and the conditions of 50° C. at the head/300 mbar operating pressure. An additional control temperature is 70° C. at the 10th stage of column C.

EXAMPLE 12 (FIG. 1)

A mixture having the composition:
n-hexane: 50.00 kg/h and
$C_{5+}$ alcohols; 50.00 kg/h
is continuously combined with tert-butanol and distilled in accordance with Example 8 under the temperatures correspond to the data provided in Example 8. Thereafter, the tert-butanol is recirculated. The withdrawal of paraffin and $C_{5+}$ alcohols takes place according to Example 8.

What is claimed is:

1. A process for the separation of a homoazeotropic mixture of a paraffin or paraffins of 6-14 carbon atoms and an alcohol or alcohols of 4-8 carbon atoms wherein the separation is conducted in a rectification system having two rectifying columns which comprises introducing a starting feed mixture containing said homoazeotropic mixture and water into a first rectifying column; effecting rectification in said first rectifying column maintained at a pressure of 50-400 mbar in the presence of water as an azeotropic agent to provide a distillate; separating the distillate, after condensation, in a phase separator into two liquid phases, one phase comprising an organic liquid phase and the other phase comprising an aqueous phase; rectifying the organic phase in a second rectifying column maintained at a pressure of 50-1,013 mbar without the addition of water into said second column; recycling an overhead product of the second rectifying column consisting of an alcohol/paraffin mixture into the first column; and obtaining the paraffin or paraffins and the alcohol or alcohols, separately, in a lower portion of one of the two rectifying columns; water present in the starting feed mixture introduced into the first rectifying column being removed from the rectification system via said phase separator.

2. A process according to claim 1, wherein additional water is supplied to the first rectifying column as an azeotropic agent when sufficient water serving as azeotropic agent is not present in the feed stream introduced as the starting feed mixture into the first rectifying column.

3. A process according to claim 1, wherein a low-boiling paraffin having a boiling point lower than the paraffin or paraffins being separated in the first rectifying column is additionally supplied as an azeotropic agent to the first column.

4. A process according to claim 1, wherein a low-boiling alcohol having a boiling point lower than the alcohol or alcohols being separated in the first column is additionally supplied as an azeotropic agent to the first rectifying column.

5. A process according to claim 1, wherein the separated paraffin or paraffins is obtained from the lower portion of the second rectifying column and the separated alcohol or alcohols is obtained in the lower portion of the first rectifying column.

6. A process according to claim 1, wherein the separated paraffin or paraffins is obtained in the lower portion of the first rectifying column and the separated alcohol or alcohols is obtained in the lower portion of the second rectifying column.

7. A process according to claim 1, wherein water is initially charged into the phase separator prior to rectification and thereafter water is introduced from the phase separator into the first rectifying column as an azeotropic agent during rectification therein.

8. A process according to claim 1, wherein the amount of water present in the first column is 1 to 1,000% by weight based on the paraffin present therein.

9. A process according to claim 1, wherein at least a part of the water, alcohol and/or paraffin, obtained after separation, is recycled into said first rectifying column.

10. A process according to claim 1, wherein the rectification system consists of said first and second rectifying columns, the same rectifying pressure is maintained in the first and second columns and water introduced into the first rectifying column is removed via said phase separator.

11. A process according to claim 1, wherein a portion of the aqueous phase separated in the phase separator is recycled into the first rectifying column.

12. A process according to claim 1, wherein the rectification system consists of said first and second rectifying columns, the same rectifying pressure being maintained in the first and second columns and water introduced into the first rectifying column being removed via said phase separator and discharged from the system.

13. A process according to claim 1, wherein the rectification system consists of said first and second rectifying columns, the same rectifying pressure is maintained in the first and second columns and water introduced into the first rectifying column is removed via said phase separator and is recycled to said first column to provide additional azeotropic agent.

* * * * *